(12) United States Patent
Diao et al.

(10) Patent No.: US 11,684,515 B2
(45) Date of Patent: Jun. 27, 2023

(54) MULTI-FIBER MULTI-SPOT LASER PROBE WITH ARTICULATING BEAM SEPARATION

(71) Applicant: Alcon Inc., Fribourg (CH)

(72) Inventors: Chenguang Diao, Irvine, CA (US); Mark Harrison Farley, Laguna Hills, CA (US); Alireza Mirsepassi, Irvine, CA (US); Ronald T. Smith, Irvine, CA (US)

(73) Assignee: Alcon Inc., Fribourg (CH)

( * ) Notice: Subject to any disclaimer, the term of this patent is extended or adjusted under 35 U.S.C. 154(b) by 339 days.

(21) Appl. No.: 17/002,914

(22) Filed: Aug. 26, 2020

(65) Prior Publication Data

US 2020/0390603 A1    Dec. 17, 2020

Related U.S. Application Data

(63) Continuation of application No. 15/900,602, filed on Feb. 20, 2018, now abandoned.
(Continued)

(51) Int. Cl.
*A61B 18/22* (2006.01)
*A61F 9/008* (2006.01)
(Continued)

(52) U.S. Cl.
CPC .......... *A61F 9/00823* (2013.01); *A61B 18/22* (2013.01); *G02B 6/3624* (2013.01);
(Continued)

(58) Field of Classification Search
CPC ....... A61F 9/00823; A61F 2009/00863; A61B 18/22; A61B 2018/2211;
(Continued)

(56) References Cited

U.S. PATENT DOCUMENTS 5,746,738 A * 5/1998 Cleary .................. A61B 18/24
606/17
6,096,028 A * 8/2000 Bahmanyar ............. A61F 9/008
606/4
(Continued)

FOREIGN PATENT DOCUMENTS

WO   WO-2010096940 A1 * 9/2010 ........ A61M 25/0169
WO   WO-2015177790 A1 * 11/2015 ........... A61B 18/245

*Primary Examiner* — Carl H Layno
*Assistant Examiner* — Michael J Lau
(74) *Attorney, Agent, or Firm* — Patterson + Sheridan, L.L.P.

(57) ABSTRACT

Multi-fiber laser probes utilize relative motion of fibers and other laser probe elements to preserve small-gauge compatibility while providing for multi-spot beam deliver, or to provide for the selectively delivery of single-spot or multi-spot beam patterns. An example probe includes fibers having distal ends that are movable as a group onto a distal ramp element affixed to a distal end of a cannula, so that the distal ends of the fibers can be moved between a retracted position, in which the distal ends of the fibers are within the cannula or ramp element, and an extended position, in which distal ends of the fibers are guided by grooves or channels of the ramp so as to extend at least partially through external openings in the distal end of the laser probe and so as to be pointed angularly away from a longitudinal axis of the cannula.

10 Claims, 8 Drawing Sheets

Related U.S. Application Data (60) Provisional application No. 62/464,464, filed on Feb. 28, 2017.

(51) Int. Cl.
*G02B 6/36* (2006.01)
*G02B 6/04* (2006.01)
*A61B 18/20* (2006.01)
*G02B 6/26* (2006.01)
*F21V 8/00* (2006.01)

(52) U.S. Cl.
CPC ............ *A61B 2018/2005* (2013.01); *A61B 2018/2025* (2013.01); *A61B 2018/2211* (2013.01); *A61B 2018/2238* (2013.01); *A61B 2018/2261* (2013.01); *A61B 2018/2266* (2013.01); *A61B 2018/2288* (2013.01); *A61F 2009/00863* (2013.01); *G02B 6/0008* (2013.01); *G02B 6/04* (2013.01); *G02B 6/262* (2013.01); *G02B 6/3636* (2013.01); *G02B 6/3644* (2013.01)

(58) Field of Classification Search
CPC .... A61B 2018/2238; A61B 2018/2261; A61B 2018/2266; A61B 2018/2288
USPC .............................................. 606/4
See application file for complete search history.

(56) References Cited

U.S. PATENT DOCUMENTS

| | | | | |
|---|---|---|---|---|
| 2002/0045811 A1* | 4/2002 | Kittrell | ............... | G02B 6/4296 606/7 |
| 2003/0125719 A1* | 7/2003 | Furnish | .................... | A61B 1/07 606/15 |
| 2004/0034290 A1* | 2/2004 | Zuluaga | ............... | A61B 5/0084 385/33 |
| 2007/0015969 A1* | 1/2007 | Feldman | ............. | A61B 5/0066 600/160 |
| 2007/0265602 A1* | 11/2007 | Mordaunt | ............... | A61F 9/008 606/4 |
| 2009/0287197 A1* | 11/2009 | Hanley | ................. | G02B 6/001 385/38 |
| 2011/0009701 A1* | 1/2011 | Feldman | ............. | A61B 5/0073 600/178 |
| 2013/0158393 A1* | 6/2013 | Papac | .................... | A61N 5/062 606/17 |
| 2015/0359595 A1* | 12/2015 | Ben Oren | .......... | A61B 18/1492 606/41 |
| 2016/0220310 A1* | 8/2016 | Taylor | ................. | A61B 18/245 |

* cited by examiner

MULTI-FIBER MULTI-SPOT LASER PROBE WITH ARTICULATING BEAM SEPARATION

PRIORITY CLAIM

This application is a continuation application of U.S. Non-Provisional patent application Ser. No. 15/900,602, and claims the benefit of priority of U.S. Provisional Patent Application Ser. No. 62/464,464 titled "MULTI-FIBER MULTI-SPOT LASER PROBE WITH ARTICULATING BEAM SEPARATION," filed on Feb. 28, 2017 (U.S. Non-Provisional patent application Ser. No. 15/900,602 claimed the benefit of priority of U.S. Provisional Patent Application Ser. No. 62/464,464), whose inventors are Chenguang Diao, Mark Harrison Farley, Alireza Mirsepassi and Ronald T. Smith, both of which are hereby incorporated by reference in their entirety as though fully and completely set forth herein.

TECHNICAL FIELD

This application relates to a laser probe for use in ophthalmic procedures and more particularly to a multi-spot laser probe for use in photocoagulation.

BACKGROUND

Laser photocoagulation therapy addresses ocular conditions such as retinal detachments and tears as well as proliferative retinopathy resulting from diseases such as diabetes. The abnormally high blood sugar in a diabetic stimulates the retinal vessels to release growth factors that in turn encourage an undesirable proliferation of blood vessels and capillaries over the retinal surface. These proliferated blood vessels are very delicate and will readily bleed into the vitreous. The body responds to the damaged vessels by producing scar tissue, which may then cause the retina to detach so as to eventually cause blindness.

In laser photocoagulation, a laser probe is used to cauterize the blood vessels at various laser burn spots across the retina. Because the laser will also damage the rods and cones that are present in the retina to allow vision, eyesight, as well as the blood vessels, is affected. Since vision is most acute at the central macula of the retina, the surgeon arranges the resulting laser burn spots in the peripheral areas of the retina. In this fashion, some peripheral vision is sacrificed to preserve central vision. During the procedure, the surgeon drives the probe with a non-burning aiming beam such that the retinal area to be photocoagulated is illuminated. Due to the availability of low-power red laser diodes, the aiming beam is generally a low-power red laser light. Once the surgeon has positioned the laser probe so as to illuminate a desired retinal spot, the surgeon activates the laser through a foot pedal or other means to then photocoagulate the illuminated area. Having burned a retinal spot, the surgeon repositions the probe to illuminate a new spot with the aiming light, activates the laser, repositions the probe, and so on until a suitable array of burned laser spots are distributed across the retina.

The number of required laser photocoagulations for any one treatment of the retina is large. For example, 1,000 to 1,500 spots are commonly burned. It may thus be readily appreciated that if the laser probe was a multi-spot probe enabling the burning of multiple spots at a time, the photocoagulation procedure would be faster (assuming the laser source power is sufficient). Accordingly, multi-spot laser probes have been developed and can be classified into two categories. A first category, denoted herein as a "multi-fiber, multi-spot" laser probe, produces its multiple laser beams through a corresponding array of optical fibers. A second category uses only a single fiber and is thus denoted herein as a "single-fiber, multi-spot" laser probe. Regardless of whether a laser probe is a single-fiber or multi-fiber probe, it should be compatible with the adapter used to connect the probes to the laser source. In that regard, it is conventional for a laser source to have a standardized interconnect such as a subminiature version A (SMA) interconnect. For example, the laser source may have a female SMA connector that receives a male SMA connector coupled to whatever instrument the laser source is driving. For a conventional single-fiber, single-spot laser probe, its male SMA connector will incorporate a single fiber. The laser source provides a focused beam known as the laser beam waist to the male SMA connector. This is quite advantageous for the single fiber probe since its optical fiber has its end face illuminated by the waist to enable efficient coupling to the laser source. But if a multi-fiber, multi-spot laser probe uses a corresponding plurality of fibers to drive its multiple spots, it cannot simply have its multiple fibers receive the focused beam from the source in this convenient single-fiber fashion because the laser waist is too narrow to couple into multiple fibers. Instead, the laser source would have to have its conventional interconnect changed or adapted so that the multiple fibers from the probe are not simply presented with the laser waist. But such changes are expensive and cumbersome.

Thus, a multi-fiber, multi-spot probe has been developed such that the laser source drives a single fiber interconnect connected to a single fiber cable that in turn drives a single-fiber/multiple-fiber optical coupling within the laser probe handpiece. The resulting optics within the handpiece increase costs because it is desirable that the laser probe be disposable to limit contamination from patient to patient. For example, the optics include a diffractive beam splitter to split the beam from the single fiber into multiple beams for distribution to the multiple fibers. To collimate the laser beam from the single fiber onto the beam splitter and then condense the resulting multiple beams onto the multiple fibers requires plano-convex lenses. But it is very difficult to move such lenses on to the laser source interconnect such that the remainder of the probe can be less expensive because of the relatively small inner diameter of such interconnects.

Another issue arises in multi-fiber, multi-spot laser probes in that the telecentric laser beams transmitted from the distal ends of the multiple fibers should be directed into different angular directions so as to properly distribute the resulting laser beam spots on the retina. To provide such distribution, a multi-fiber, multi-spot laser probe has been developed with the distal ends of the fibers bent into the desired angular directions. But such bending is cumbersome and increases costs as well.

To avoid the issues associated with the use of multiple fibers, the light beam from a single-fiber laser probe can be directed onto a diffractive beam splitter that splits the beam into multiple diffracted beams for transmission to the retina. However, the diffractive beam splitter must then focus the resulting diffracted beams, which requires the grating prescription to be spatially varying across the element. Not only does such a complication increase costs, the resulting spatially-varying diffractive beam splitter will reduce the overall performance. Such a design also makes varying the distance between the distal fiber end the diffractive element difficult.

Accordingly, there is a need in the art for improved multi-spot laser probes.

SUMMARY

Several embodiments of the multi-fiber laser probes disclosed herein utilize relative motion of fibers and other laser probe elements to preserve small-gauge compatibility while providing for multi-spot beam deliver, or to provide for the selectively delivery of single-spot or multi-spot beam patterns.

An example probe according to some embodiments includes fibers having distal ends that are movable as a group onto a distal ramp element affixed to a distal end of a cannula, so that the distal ends of the fibers can be moved between a retracted position, in which the distal ends of the fibers are within the cannula or ramp element, and an extended position, in which distal ends of the fibers are guided by grooves or channels of the ramp element so as to extend at least partially through external openings in the distal end of the laser probe and so as to be pointed angularly away from a longitudinal axis of the cannula.

Another example probe comprises a plurality of fibers extending from a proximal end of the laser probe to at least near a distal end of the laser probe, where the proximal end of the laser probe is configured to be coupled to a laser source via an adapter interface, a cannula having a distal end and surrounding the plurality of fibers along at least a portion of the laser probe at or near the distal end of the laser probe, and a ramp element extending from the distal end of cannula and situated between the plurality of fibers, and having a groove corresponding to each of the fibers. In this example, the cannula and ramp element are together translatable in a longitudinal direction, relative to the fibers, between a distally extended position, in which the distal ends of the fibers are completely within or substantially completely within the cannula, and a proximally retracted position, in which the distal ends of the fibers are guided by the grooves of the ramp element so as to extend outside of the cannula and so as to be pointed angularly away from a longitudinal axis of the cannula.

Another example of a multi-fiber, multi-spot, laser probe, comprises a plurality of fibers extending from a proximal end of the laser probe to at least near a distal end of the laser probe, where the proximal end of the laser probe is configured to be coupled to a laser source via an adapter interface, and a cannula having a distal end and surrounding the plurality of fibers along at least a portion of the laser probe at or near the distal end of the laser probe. This example probe further comprises a ramp element affixed to the distal end of cannula and having a groove and/or channel corresponding to each of the fibers and extending to the distal end of the laser probe, as well as a sleeve extending within at least a portion of the cannula and translatable, within the cannula. In these embodiments, the plurality of fibers are longitudinally fixed, relative to the cannula and ramp element, so that distal ends of the fibers are at or near a distal end of the ramp element, and the sleeve is translatable between a proximally retracted position, in which the distal ends of the fibers are oriented so as to point in a direction substantially parallel to a longitudinal axis of the cannula, and a distally extended position, in which the distal ends of the fibers are moved and constrained by the sleeve and the grooves or channels of the ramp so as to be pointed angularly away from the longitudinal axis of the cannula.

Still another example of a multi-fiber, multi-spot, laser probe likewise comprises a plurality of fibers extending from a proximal end of the laser probe to near a distal end of the laser probe, where the proximal end of the laser probe is configured to be coupled to a laser source via an adapter interface, and a cannula having a distal end and surrounding the plurality of fibers along at least a portion of the laser probe at or near the distal end of the laser probe. This example, however, comprises a lens array element arranged in or at the distal end of the cannula, the lens array element comprising an array of lensing elements disposed angularly around a first face of the lens array element, where the first face faces towards distal ends of the fibers, within the cannula. The lens array element is rotatable, in this example, relative to the plurality of fibers, from a first position, in which each of the lensing elements is arranged between the distal end of a corresponding one of the fibers and the distal end of the laser probe, to a second position, in which substantially planar regions of the first face of the lens array element are arranged between the distal ends of each of the fibers and the distal end of the laser probe. In some embodiments according to this example, the lensing elements comprise micro-lens elements disposed on the first face of the lens array element. In other embodiments, the lens array element is instead a wedge array element, comprising a plurality of micro-wedge elements disposed angularly around a first face of the wedge array element, in a manner similar to the lens array element summarized above.

DETAILED DESCRIPTION

Described in detail herein are improved multi-fiber, multi-spot laser probes that are compatible with conventional laser source interconnects.

Figure 1:
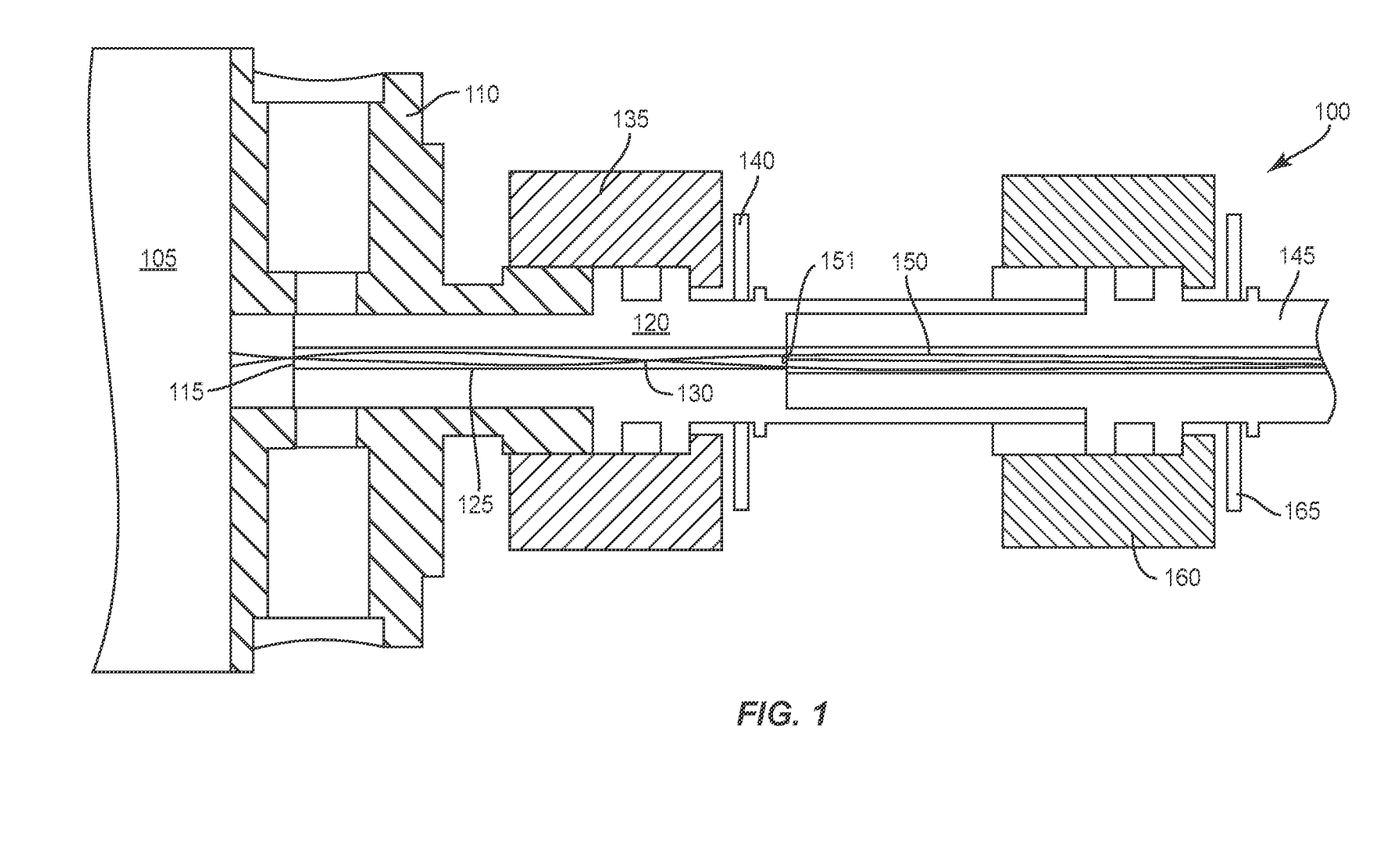
FIG. 1 is a longitudinal cross-sectional view of a laser source coupled to an adapter element containing a gradient-index (GRIN) lens for coupling to a proximal end of a multi-fiber, multi-spot laser probe.

Turning now to the drawings, certain details of a multi-fiber, multi-spot laser probe 100 are shown in FIG. 1. Not shown in FIG. 1 are details of the proximal end of laser probe 100; details of several realizations of the proximal end are provided below. The portions of the multi-fiber, multi-spot laser probe 100 shown in FIG. 1 are also illustrated in U.S. Pat. No. 8,951,244; thus, it will be appreciated that the details shown in FIG. 1 represent an example of the prior art.

Returning to FIG. 1, it can be seen that a laser source 105 drives probe 100 through a suitable interconnect. A common standardized interconnect for laser source 105 is a subminiature version A (SMA) adapter. Thus, laser source 105 includes a female SMA adapter 110. However, it will be appreciated that laser probe 100 is readily adapted to mate with any conventional standardized optical interconnect so long as the laser source's interconnect presents a focused beam spot such as laser waist 115 to a proximal end of a male connector from the laser probe. Thus, the following discussion will assume that laser probe 100 couples to source 105 through a customized SMA adapter 120 without loss of generality.

To receive laser waist 115, the bore of SMA adapter 120 includes a gradient index (GRIN) lens 125. GRIN lens 125 may be a simple, single-element cylindrical GRIN rod lens that is readily inserted into such a bore. GRIN lens 125 is designed to relay the focused beam to a second focused spot 130 and then to a collimated beam wave front at its distal end. As known in the SMA arts, SMA adapter 120 secures to SMA adapter 110 through a threaded cylinder 135 and retaining ring 140. SMA adapter 120 has both a male end for insertion into SMA adapter 110 but also a female end that receives a conventional optical interconnect such a male SMA 905 fiber connector 145. Connecter 145 secures to adapter 120 through a threaded cylinder or ring 160 and retaining ring 165. Connector 145 includes in its bore an array of optical fibers 150. A proximal end 151 of array 150 is separated from the distal end of GRIN lens 125 by a suitable air gap such as a 220 µm air gap. Connector 145 connects to a flexible cable encasing fibers 150 that leads to a handpiece and cannula, as known in the laser probe arts.

Figure 2:
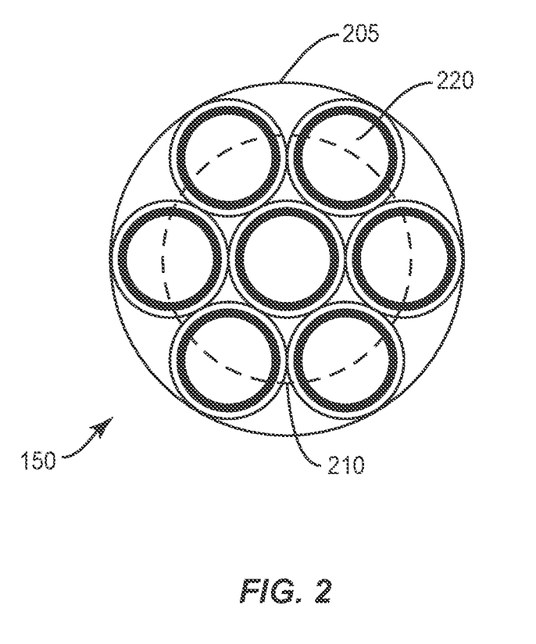
FIG. 2 shows a radial cross-sectional view of a multi-fiber array within the proximal end of the probe of FIG. 1.

An example embodiment of fiber array 150 is shown in cross-section in FIG. 2. The laser beam boundary at the proximal end 151 of FIG. 1 is shown for both a green laser beam boundary 205 from source 105 as well as a red aiming beam boundary 210. Array 150 includes a central fiber circumferentially surrounded by six outer fibers. In one embodiment, each fiber 220 has a numerical aperture (NA) of 0.22 achieved through a 75 µm glass core encased in a 90 µm cladding, surrounded by a 101 µm jacket. To minimize the amount of uncoupled laser energy into array 150, GRIN lens 125 is configured such that laser beam boundary 205 just encompasses the six outer fibers. The clocking of array 150 relative to the laser beam is not an issue as the laser beam and array 150 are at least generally axisymmetric. Array 150 extends to a distal end of the laser probe; details of several embodiments of the distal end of the laser probe are discussed in more detail below.

The advantageous properties of such a proximal interconnection in that no complicated, multi-lens relay system is required. Instead, GRIN lens 125 is readily inserted into the bore of adapter 120 that enables a standardized adapter such as male SMA adapter 145 to attach a disposable laser probe receiving fiber array 150. Without GRIN lens 125 and its adapter 120, standardized adapter 110 on laser source 105 would have to be changed, which is plainly undesirable since other attachments for source 105 would have to change in concert. Alternatively, the source's adapter could be left standardized but then a multi-lens relay system would be required. However, SMA adapter 120 and GRIN lens 125 eliminate such complications. Although SMA adapter 120 is thus quite advantageous, one can appreciate that roughly 50% of the laser energy is delivered to the interstices between the fibers in array 150 as seen in FIG. 2. This laser energy is thus unavailable for use in photocoagulation, thereby increasing the necessary laser source power and/or the amount of time necessary to produce the laser burn spots.

Figure 3:
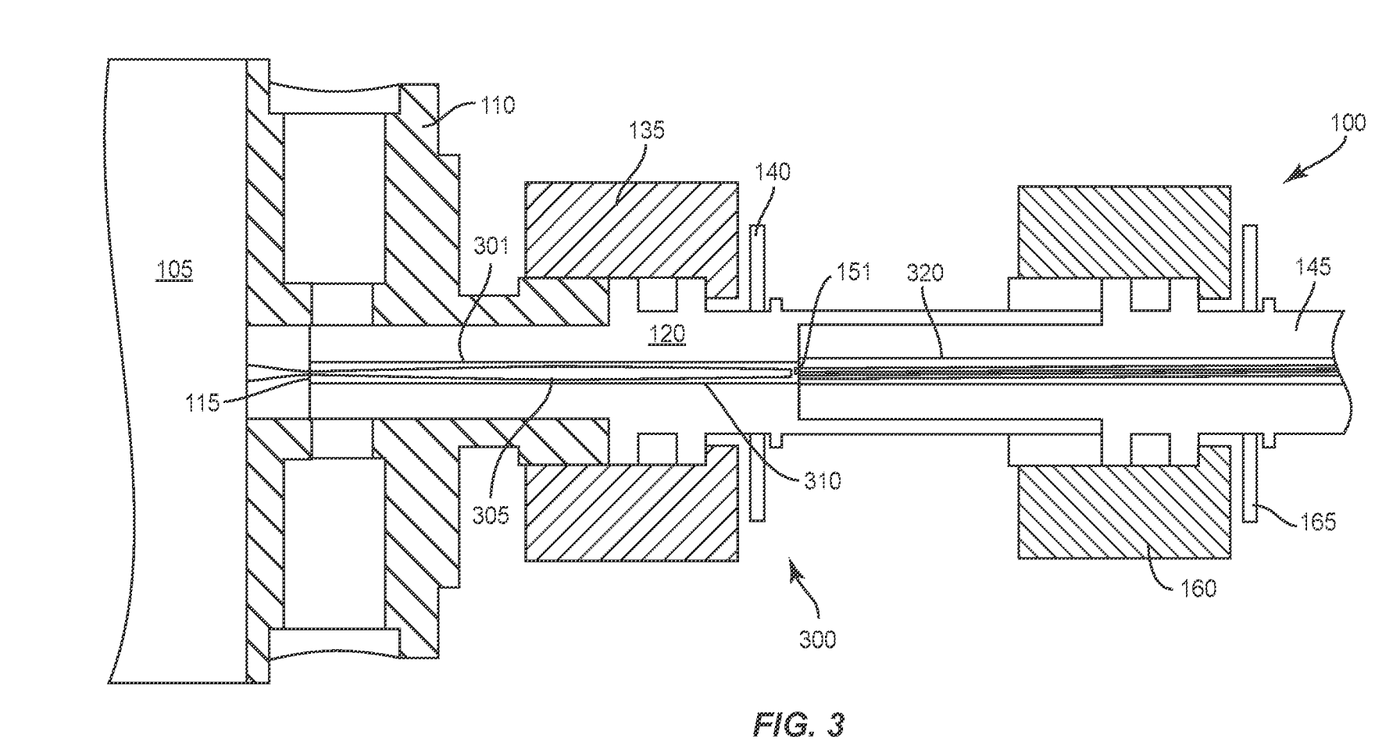
FIG. 3 is a longitudinal cross-sectional view of a laser source coupled to an adapter element including a diffractive beam splitter for coupling to a proximal end of a multi-fiber, multi-spot laser probe.
Figure 4:
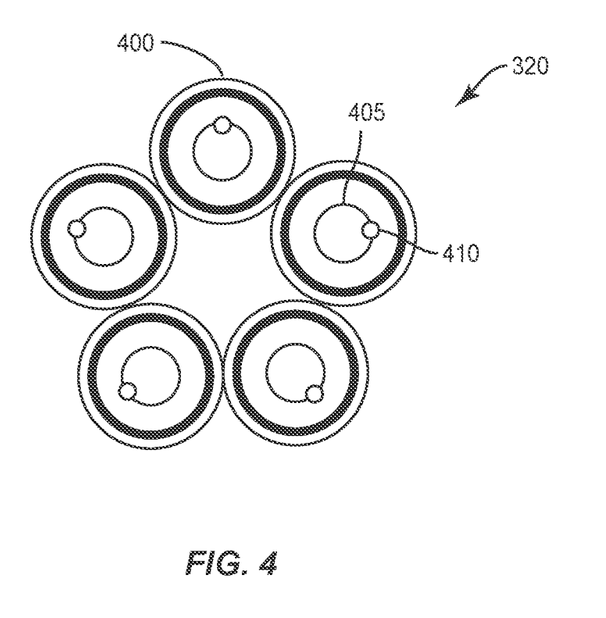
FIG. 4 is a radial cross-sectional view of a multi-fiber array within the proximal end of the probe of FIG. 3.

Turning now to FIG. 3, a diffractive embodiment that does not illuminate fiber array interstices is illustrated. As discussed with regard to FIG. 1, customized SMA adapter 120 permits a user to conveniently attach a disposable probe to adapter 120 to drive laser energy onto a fiber array. In the embodiment shown in FIG. 1, however, adapter 120 includes in its bore a diffractive beam splitter 305 arranged between a first GRIN lens 301 and a second GRIN lens 310. GRIN lens 301 is configured to collimate the laser beam diverging from laser waist 115 into a collimated wave front presented to diffractive beam splitter 305. GRIN lens 310 is configured to focus the resulting diffracted multiple laser beams from splitter 305 onto a proximal face 151 of a fiber array 320 contained within the bore of male SMA adapter 145. Fiber array 320 includes a plurality of fibers arranged according to the diffractive properties of diffractive beam splitter 305. For example, if diffractive beam splitter produces a symmetric pentagonal distribution of five diffracted beams, fiber array 320 is arranged in a corresponding pentagonal distribution. FIG. 4 shows such an arrangement for fiber bundle 320 at its proximal face 151.

In one embodiment, each optical fiber 400 has a 75 µm glass core clad in a 90 µm cladding, which in turn is surrounded by a 101 µm jacket, to achieve an NA of 0.22. The resulting projection of the diffracted green laser beams from splitter 305 is indicated by a boundary 405. Because diffraction is wavelength dependent, the projection of the aiming beam will have a different alignment with fiber array 320. Thus, splitter 305 and fiber array 320 are arranged such that boundary 405 is axially aligned with each fiber 400, whereas a boundary 410 of a red aiming beam is radially displaced with regard to a center or longitudinal axis of each fiber.

In one embodiment, the off-axis displacement provided by splitter 305 to each green diffracted beam is 1.45 degrees. GRIN lens 310 focuses the resulting collimated and diffracted beams onto the entrance face of each fiber 400 in array 320. By such an appropriate clocking of array 320 relative to the diffracted beams, efficient coupling of the respective diffracted beam and the aiming beam into each fiber 400 is achieved. In that regard, other types of adapters such as a ferrule connector (FC) or a standard connector (SC) commonly used in the telecommunications industry may be used instead of SMA adapter 120 to assist in optimal clocking. As discussed with regard to FIG. 1, assembly of the optical components into SMA adapter 120 is advantageously convenient in that GRIN lenses 301 and 310 as well as intervening diffractive beam splitter 305 may have optical adhesive applied and then slid into the bore of adapter 120 and abutted end-to-end with each other. In contrast, an alignment of refractive lenses would be cumbersome and difficult in comparison.

Figure 5:
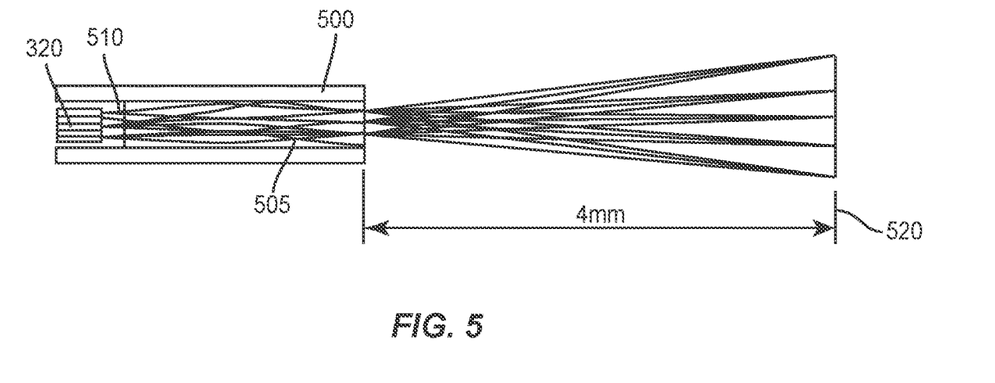
FIG. 5 illustrates a GRIN lens for angularly separating the projected multiple beams emitted from the multi-fiber array of FIG. 4.

With the laser beam from the source split and telecentrically propagated through the fiber array as discussed above with regard to either FIG. 1 or FIG. 3, there remains the issue of angularly projecting focused laser spots from the laser probe. U.S. Pat. No. 8,951,244 disclosed a GRIN lens solution, an example of which is shown in FIG. 5. It will be appreciated that while the example embodiment shown in FIG. 5 is particularly adapted for compatibility with the fiber array 320 of FIG. 3, it will be appreciated that an analogous embodiment can be readily constructed for fiber array 150 of FIG. 1.

As seen in FIG. 5, a laser probe cannula 500, e.g., a stainless-steel cannula, receives a GRIN lens 505 at its distal end. A distal end of fiber array 320 is displaced within the cannula so as to project diverging beams 510 at a proximal end face of GRIN lens 505. GRIN lens 505 then focuses the beams on the retinal surface 520. The distribution of the resulting focused beams on the retina depends on the distribution of the fibers at the distal end of array 320.

In that regard, whereas the distribution at the proximal end of array 320 (FIG. 3) should be axially symmetric, one can arrange the fibers in any suitable distribution at the distal end. For example, as seen in FIG. 5, array 320 is linearly arranged at the distal end. The resulting laser spots are thus an enlarged version of the image (in this embodiment, a linear array) presented to GRIN lens 505. In one embodiment, GRIN lens 505 focuses the angularly-distributed beams at a distance of 4 mm from the distal end of cannula 500. Advantageously, GRIN lens 505 obviates any need for: bending the fibers into the desired angular distribution (and the associated problems of such bending), beveling the distal end faces of the fibers, or adding optical elements to the distal end faces. The fibers can even be touching one another in array 320 and GRIN lens 505 will still be effective.

In the following, several alternatives to the configuration shown in FIG. 5 for the distal end of a multi-fiber laser probe are described in detail. These embodiments have in common that the GRIN lens 505 is removed from the laser beam path at the probe's distal end, and several embodiments have no optical elements distal to the optical fibers. Test data have shown certain GRIN lens materials to be susceptible to thermal failure due to increased absorption caused by photodarkening and/or moisture ingress through the anti-reflective coating. The increased absorption leading to this failure mode is associated with certain GRIN lens chemistries, and may be alleviated by embodiments that eliminate the use of optics distal to the laser transmission optical fibers, or that use distal optics made from non-GRIN materials, such as pure fused silica. It will be appreciated, then, that the several embodiments detailed herein may improve thermal reliability, while providing optical performance similar to the device shown in FIG. 5.

The embodiments detailed below further provide a variety of actuation means to induce angular beam separation, via fiber curvature. Various embodiments provide advantages such as small-gauge compatibility and/or switchable quasi-single-spot and multi-spot beam delivery.

The several embodiments detailed below are presented with respect to 4-fiber or 5-fiber embodiments of the invention, which are shown in axial and transverse cross section views. It will be understood, however, that the number of fibers is not limited to 4 or 5—fewer or more fibers may be used, in various embodiments. Further, the embodiments are not presented in any particular order. The embodiments disclosed herein may be implemented in laser probes that are compatible with either of the adapters described above, i.e., in FIGS. 1 and 3, which provide means for splitting the beam and focusing the resulting multiple beams into the proximal ends of optical fibers, such each fiber carries its own beam. It will be understood, however, that the embodiments described below may be implemented in laser probes having different mating configurations at the proximal end, and/or in conjunction with different adapters or interfaces for coupling a laser source or sources to the multiple fibers of the multi-fiber laser probe.

Figure 6A:
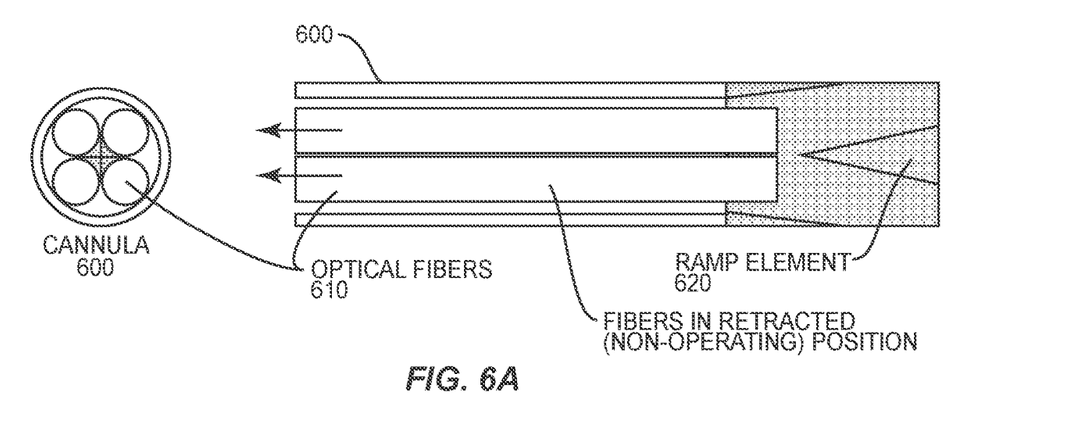
FIG. 6A illustrates an example embodiment of a distal end of a multi-fiber multi-spot laser probe that incorporates a spreading spacer at the distal end of the laser probe, configured so that fibers in the probe can be slid from a retracted, non-operating position to an extended operating position.
Figure 6B:
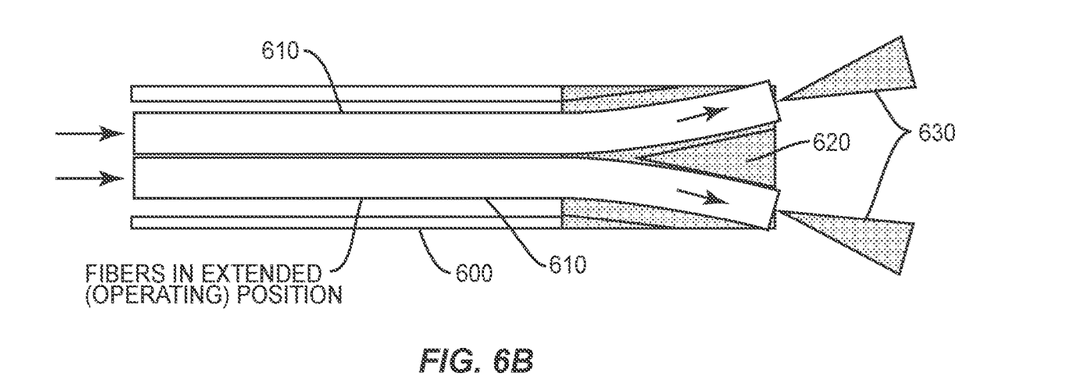
FIG. 6B illustrates an example embodiment of a distal end of a multi-fiber multi-spot laser probe that incorporates a spreading spacer at the distal end of the laser probe, configured so that fibers in the probe can be slid from a retracted, non-operating position to an extended operating position.

A first example embodiment of the distal end of a multi-fiber multi-spot laser probe that omits a GRIN lens at the distal end is shown in FIGS. 6A and 6B. As seen in the figures, this example laser probe includes fibers 610 with cleaved or polished ends that are movable as a group onto a distal ramp element 620, so that the fibers 610 can be moved between two states. A first state is shown in FIG. 6A, which illustrates a retracted, non-operating position, which provides a compact outer diameter for insertion and extraction, e.g., through small-gauge trocar entry systems. FIG. 6B illustrates an extended, operating position, in which the fibers 610 have been translated towards the distal end of the laser probe and are forced by ramp element 620 to curve outward and at least partially through external openings in the distal end of the laser probe, for delivering angularly separated beams 630 to achieve a multi-spot pattern.

As seen in FIGS. 6A and 6B, ramp element 620 fits into or onto the distal end of cannula 600, which surrounds the fibers 600 along at least the illustrated portion of the laser probe, i.e., at or near the distal end of the laser probe. Ramp element 620 may be formed from a separate machined component having four angled holes converting at its proximal end and diverging distally, which are of sufficient size to allow passage of the fibers. The ramp element may also be manufactured by additive or subtractive microfabrication processes. It will be appreciated that ramp element 620 comprises a channel and/or groove, for each of the fibers 610, such that the fibers 610 are guided by the channels and/or grooves when the fibers 610 are translated towards the distal end, and thus into the extended position, and when the fibers are retracted, towards the proximal end of the probe (not shown), into the retracted position.

It will be appreciated, then, that the laser probe illustrated in FIGS. 6A and 6B is an example of a multi-fiber, multi-spot, laser probe that comprises a plurality of fibers 610 extending from a proximal end of the laser probe to at least near a distal end of the laser probe, where the proximal end of the laser probe is configured to be coupled to a laser source via an adapter interface, and a cannula 600 having a distal end and surrounding the plurality of fibers 610 along at least a portion of the laser probe at or near the distal end of the laser probe. The illustrated probe further comprises a ramp element 620 affixed to the distal end of the cannula and having a groove and/or channel corresponding to each of the fibers 610 and extending to the distal end of the laser probe. The plurality of fibers 610 are translatable in a longitudinal direction, relative to the cannula 600 and ramp element 620, between a retracted position, in which the distal ends of the fibers 610 are within the cannula 600 and/or ramp element 620, and an extended position, in which the distal ends of the fibers 610 are guided by the grooves or channels of the ramp element 620 so as to extend at least partially through external openings in the distal end of the laser probe and so as to be pointed angularly away from a longitudinal axis of the cannula 600. The plurality of fibers 610 may be extended and retracted by means of a manual actuator having a sliding element positioned at a suitable location on the probe to be moved by a thumb or finger of the surgeon's grasping hand, or alternatively by a powered actuator.

Figure 7A:
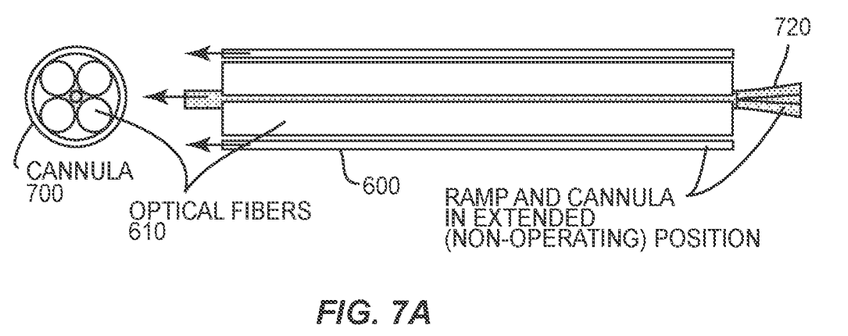
FIG. 7A illustrates an example embodiment of a distal end of a multi-fiber multi-spot laser probe that incorporates a retracting cannula portion and a distal spreading spacer.
Figure 7B:
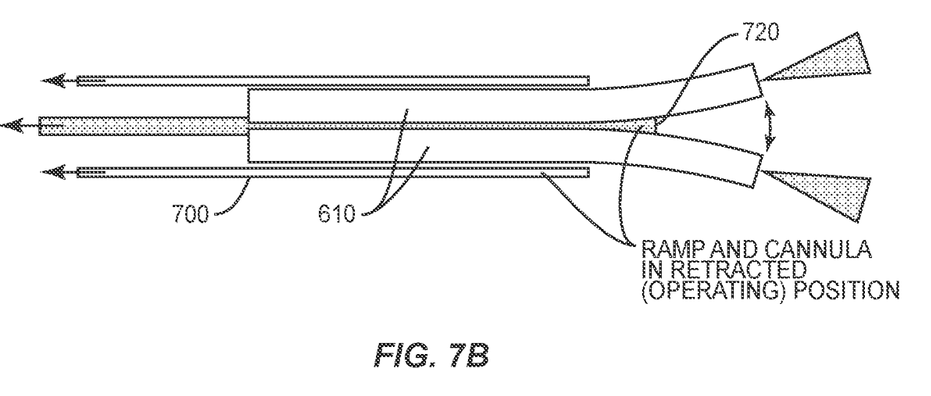
FIG. 7B illustrates an example embodiment of a distal end of a multi-fiber multi-spot laser probe that incorporates a retracting cannula portion and a distal spreading spacer.

FIGS. 7A and 7B illustrate another embodiment, which also includes cleaved or polished fibers 610 as well as an external distal ramp element 720. Distal ramp element 720 is similar to the ramp element 620 in FIGS. 6A and 6B, but in the laser probe embodiment shown in FIGS. 7A and 7B, the fibers 610 are axially fixed in position relative to a handpiece (not shown). In the laser probe shown in FIGS. 7A and 7B, the cannula 700 and ramp element 720 are movable relative to the fibers 610 (and handpiece), again so as to provide two distinct states. A first state is shown in FIG. 7A, which illustrates a retracted, non-operating position, which provides a compact outer diameter for insertion and extraction, e.g., through small-gauge trocar entry systems. FIG. 7B illustrates an extended, operating position, in which the fibers 610 have been translated towards the distal end of the laser probe and are forced by ramp element 720 to curve outward, external to cannula 700. Again, when in the position shown in FIG. 7B, the ends of fibers 610 are oriented to deliver angularly separated beams, to achieve a multi-spot pattern. As seen in the figures, ramp element 720 comprises a groove for each of the fibers 610, such that the fibers 610 are separated from one another and guided by the grooves when the fibers 610 are translated towards the distal end, and thus into the extended position, and when the fibers are retracted, towards the proximal end of the probe (not shown), into the retracted position. The cannula 700 and ramp element 720 may be extended and retracted by means of a manual actuator having a sliding element positioned at a suitable location on the probe so as to be moved by a thumb or finger of the surgeon's grasping hand, or alternatively by a powered actuator.

The laser probe illustrated in FIGS. 7A and 7B may thus be understand as an example of a multi-fiber, multi-spot laser probe that comprises a plurality of fibers 610 extending from a proximal end of the laser probe to at least near a distal end of the laser probe, where the proximal end of the laser probe is configured to be coupled to a laser source via an adapter interface, a cannula 700 having a distal end and surrounding the plurality of fibers 610 along at least a portion of the laser probe at or near the distal end of the laser probe, and a ramp element 720 extending from the distal end of cannula 700 and situated between the plurality of fibers 610, and having a groove corresponding to each of the fibers 610. In this example, the cannula 700 and ramp element 720 are together translatable in a longitudinal direction, relative to the fibers 610, between a distally extended position, in which the distal ends of the fibers 610 are completely within or substantially completely within the cannula 700, and a proximally retracted position, in which the distal ends of the fibers 610 are guided by the grooves of the ramp element 720 so as to extend outside of the cannula 700 and so as to be pointed angularly away from a longitudinal axis of the cannula 700.

Figure 8:
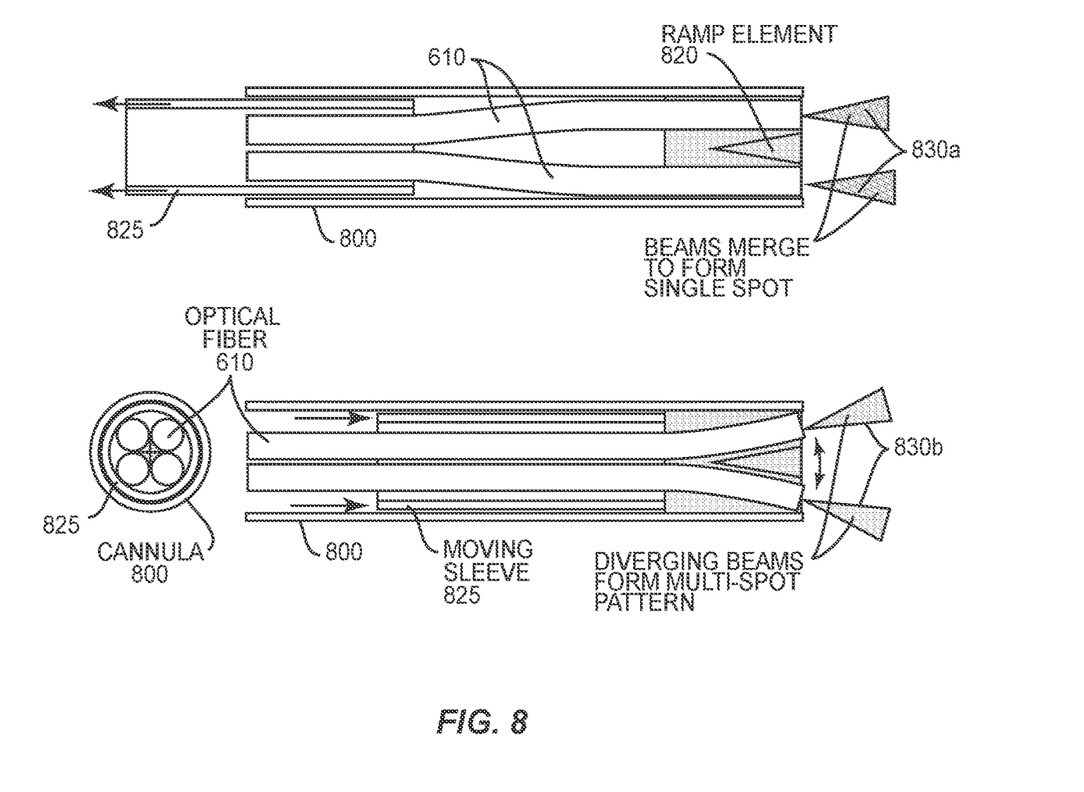
FIG. 8 illustrates an example embodiment of a distal end of a multi-fiber multi-spot laser probe that incorporates a moving sleeve, within a distal cannula portion, and a distal spreading spacer, configured to switch light deliver from a single-spot mode to a multi-spot mode.

FIG. 8 illustrates an embodiment that, like those shown in FIGS. 6A, 6B, 7A, and 7B, comprises cleaved or polished fibers 610, and further includes a distal ramp element 820, which is similar to the distal ramp element in the embodiments shown in FIGS. 6A and 6B. In the embodiment shown in FIG. 8, however, the fibers 610 are axially fixed in position, relative to the cannula 800 and distal ramp 820. A sleeve 825, which is within cannula 800 and movable (i.e., translatable) relative to cannula 800, induces fiber curvature in the radial direction when extended along the outer surfaces of the fibers 610, drawing them together. This action, coupled with the guiding action of grooves/channels in distal ramp element 820, results in angularly separated beams 830b from each of the fibers 610, as shown in the bottom portion of FIG. 8. When the moving sleeve 825 is retracted, the fibers 610 can revert to a straight condition at the distal tip, resulting in substantially parallel beams 830a that merge into a single spot, as shown in the top portion of FIG. 8. In this manner, the probe can be switched from multi-spot delivery, when the sleeve 825 is extended in the distal direction, to single-spot delivery, when the sleeve 825 is retracted.

Accordingly, the embodiment shown in FIG. 8 may be understood as an example of a multi-fiber, multi-spot, laser probe that comprises a plurality of fibers 610 extending from a proximal end of the laser probe to at least near a distal end of the laser probe, where the proximal end of the laser probe is configured to be coupled to a laser source via an adapter interface, and a cannula 800 having a distal end and surrounding the plurality of fibers 610 along at least a portion of the laser probe at or near the distal end of the laser probe. This example probe further comprises a ramp element 820 affixed to the distal end of cannula 800 and having a groove and/or channel corresponding to each of the fibers 610 and extending to the distal end of the laser probe, as well as a sleeve 825 extending within at least a portion of cannula 800 and translatable, within cannula 800. In these embodiments, the plurality of fibers 610 are longitudinally fixed, relative to cannula 800 and ramp element 820, so that distal ends of the fibers 610 are at or near a distal end of the ramp element 820, and the sleeve 825 is translatable between a proximally retracted position, in which the distal ends of the fibers 610 are oriented so as to point in a direction substantially parallel to a longitudinal axis of cannula 800, and a distally extended position, in which the distal ends of the fibers 610 are moved and constrained by the sleeve 825 and the grooves or channels of the ramp element 820 so as to be pointed angularly away from the longitudinal axis of the cannula 800.

Figure 9:
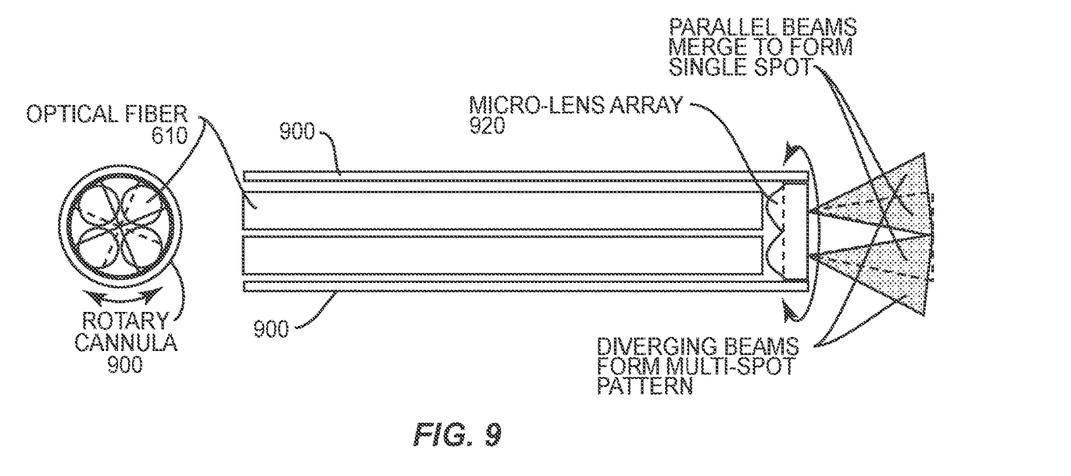
FIG. 9 illustrates an embodiment that incorporates a rotary-selectable micro-lens array.
Figure 10:
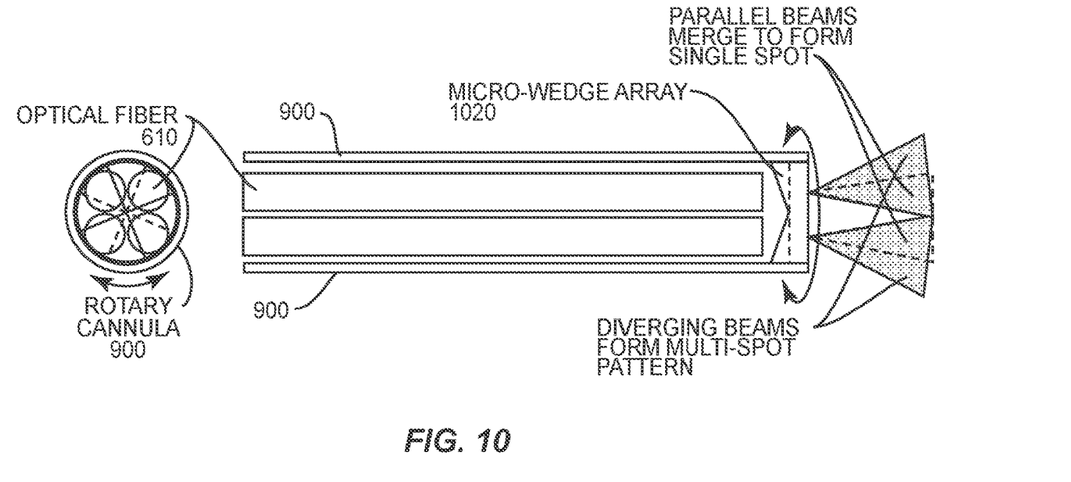
FIG. 10 illustrates an embodiment that incorporates a rotary-selectable micro-lens array.

The embodiments in FIGS. 9 and 10 provide the advantages of selectable lens or wedge optics, to provide either a diverging 4-spot beam pattern or a pattern of 4 parallel beam that merge to form essentially a single spot. In these embodiments, this is accomplished by a second set of facets that provide alternating flat window regions, facing away from the distal end of the probe, at substantially 45° rotational offsets from the lens or wedge array elements, which are arranged around the micro-lens 920, as shown in FIG. 9, or the wedge array 1020, as shown in FIG. 10. In this manner, the probe can be switched from multi-spot delivery to single-spot delivery by rotating the cannula 900 and distal micro-lens 920 or wedge array 1020, relative to the fibers, by approximately 45°.

Thus, the embodiments shown in FIGS. 9 and 10 may be understood as examples of a multi-fiber, multi-spot, laser probe that, like the examples shown in FIGS. 6-8, include a plurality of fibers 610 extending from a proximal end of the laser probe to near a distal end of the laser probe, wherein the proximal end of the laser probe is configured to be coupled to a laser source via an adapter interface, and a cannula 900 having a distal end and surrounding the plurality of fibers 610 along at least a portion of the laser probe at or near the distal end of the laser probe. These examples, however, further include a lens array element 920 or 1020 arranged in or at the distal end of the cannula 900 and comprising an array of lensing elements disposed angularly around a first face of the lens array element 920 or 1020, the first face facing towards distal ends of the fibers, within the cannula 900. The lens array element 920 or 1020 is rotatable, relative to the plurality of fibers 610, from a first position, in which each of the lensing elements is arranged between the distal end of a corresponding one of the fibers 610 and the distal end of the laser probe, to a second position, in which substantially planar regions of the first face of the lens array element 920 or 1020 are arranged between the distal ends of each of the fibers 610 and the distal end of the laser probe. In some embodiments, for example, the lens array element 920 is affixed to the cannula 900 and the cannula 900 is rotatable, relative to the plurality of fibers 610, along with the lens array element 920.

Embodiments described above illustrate but do not limit the invention. It should also be understood that numerous modifications and variations are possible in accordance with the principles of the present invention.

What is claimed is:

1. A multi-fiber, multi-spot laser probe, comprising:
    a plurality of fibers extending from a proximal end of the laser probe to at least near a distal end of the laser probe, wherein the proximal end of the laser probe is configured to be coupled to a laser source;
    a cannula having a distal end and surrounding the plurality of fibers along at least a portion of the laser probe at or near the distal end of the laser probe; and
    a ramp element affixed to the distal end of the cannula and having a groove and/or channel corresponding to each of the fibers and extending to the distal end of the laser probe;
    wherein the ramp element or plurality of fibers are translatable in a longitudinal direction, relative to the other of the ramp element or plurality of fibers, between a retracted position, in which the distal ends of the fibers are within the cannula and/or ramp element, and an extended position, in which the distal ends of the fibers are guided by the grooves or channels of the ramp element so as to extend at least partially through external openings in the distal end of the laser probe and so as to be pointed angularly away from a longitudinal axis of the cannula.

2. The multi-fiber, multi-spot laser probe of claim 1, wherein the laser probe is configured to be coupled to a laser source via an adapter interface.

3. The multi-fiber, multi-spot laser probe of claim 1, wherein the cannula and ramp element are together translatable in a longitudinal direction, relative to the fibers, between a distally extended position, in which the distal ends of the fibers are completely within or substantially completely within the cannula, and a proximally retracted position, in which the distal ends of the fibers are guided by the grooves of the ramp element so as to extend outside of the cannula and so as to be pointed angularly away from a longitudinal axis of the cannula.

4. The multi-fiber, multi-spot laser probe of claim 1, further comprising:
    a sleeve extending within at least a portion of the cannula and translatable, within the cannula;
    wherein the plurality of fibers are longitudinally fixed, relative to the cannula and ramp element, so that distal ends of the fibers are at or near a distal end of the ramp element, and wherein the sleeve is translatable between a proximally retracted position, in which the distal ends of the fibers are oriented so as to point in a direction substantially parallel to a longitudinal axis of the cannula, and a distally extended position, in which the distal ends of the fibers are moved and constrained by the sleeve and the grooves or channels of the ramp element so as to be pointed angularly away from the longitudinal axis of the cannula.

5. The multi-fiber, multi-spot laser probe of claim 4, wherein the distal ends of the fibers are arranged, when the sleeve is in the proximally retracted position, so that light beams emitted from the distal ends of the fibers merge to form a single spot at working distances equal to or greater than the distance at which the beams converge.

6. The multi-fiber, multi-spot laser probe of claim 1, further comprising:
    a lens array element arranged in or at the distal end of the cannula and comprising an array of lensing elements disposed angularly around a first face of the lens array element, the first face facing towards distal ends of the fibers, within the cannula;
    wherein the lens array element is rotatable, relative to the plurality of fibers, from a first position, in which each of the lensing elements is arranged between the distal end of a corresponding one of the fibers and the distal end of the laser probe, to a second position, in which substantially planar regions of the first face of the lens array element are arranged between the distal ends of each of the fibers and the distal end of the laser probe.

7. The multi-fiber, multi-spot laser probe of claim 6, wherein the lens array element is affixed to the cannula and the cannula is rotatable, relative to the plurality of fibers, along with the lens array element.

8. The multi-fiber, multi-spot laser probe of claim 6, wherein the lensing elements comprise micro-lens elements disposed on the first face of the lens array element.

9. The multi-fiber, multi-spot laser probe of claim 6, wherein the distal ends of the fibers and the lensing elements of the lens array element are arranged so that when the lens array element is in the second position, light beams emitted from the distal ends of the fibers merge to form a single spot at working distances equal to or greater than the distance at which the beams converge, and so that when the lens array element is in the first position, light beams emitted from the distal ends of the fibers form a corresponding plurality of spots at the working distance.

10. The multi-fiber, multi-spot laser probe of claim 1, further comprising:
    a wedge array element arranged in or at the distal end of the cannula and comprising an array of micro-wedge elements disposed angularly around a first face of the lens array element, the first face facing towards distal ends of the fibers, within the cannula;
    wherein the wedge array element is rotatable, relative to the plurality of fibers, from a first position, in which each of the micro-wedge elements is arranged between the distal end of a corresponding one of the fibers and the distal end of the laser probe, to a second position, in which substantially planar regions of the first face of the lens array element are arranged between the distal ends of each of the fibers and the distal end of the laser probe.

* * * * *